US010881832B2

United States Patent
Chu (10) Patent No.: US 10,881,832 B2
(45) Date of Patent: Jan. 5, 2021

(54) MEDICAL SYSTEMS, DEVICES, AND RELATED METHODS

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 367 days.

(21) Appl. No.: 15/793,085

(22) Filed: Oct. 25, 2017

(65) Prior Publication Data

US 2018/0117280 A1    May 3, 2018

Related U.S. Application Data

(60) Provisional application No. 62/415,206, filed on Oct. 31, 2016.

(51) Int. Cl.
| | | |
|---|---|---|
| A61B 1/00 | (2006.01) | |
| A61B 1/005 | (2006.01) | |
| A61B 1/018 | (2006.01) | |
| A61M 25/01 | (2006.01) | |
| G02B 23/24 | (2006.01) | |
| A61B 1/012 | (2006.01) | |

(Continued)

(52) U.S. Cl.
CPC ....... *A61M 25/0133* (2013.01); *A61B 1/0014* (2013.01); *A61B 1/0051* (2013.01); *A61B 1/0052* (2013.01); *A61B 1/00066* (2013.01); *A61B 1/00124* (2013.01); *A61B 1/00126* (2013.01); *A61B 1/00128* (2013.01); *A61B 1/012* (2013.01); *A61B 1/015* (2013.01); *A61B 1/018* (2013.01); *A61B 1/307* (2013.01); *G02B 23/24* (2013.01); *A61B 2017/00389* (2013.01); *A61B 2017/00455* (2013.01)

(58) Field of Classification Search
CPC ....... A61B 1/0014; A61B 1/015; A61B 1/018; A61B 2017/00389; A61B 2017/00455
USPC ........................................................ 600/136
See application file for complete search history.

(56) References Cited

U.S. PATENT DOCUMENTS 5,413,107 A    5/1995  Oakley et al.
5,702,349 A *  12/1997 Morizumi .......... A61B 1/00188
                                                                600/131
(Continued)

FOREIGN PATENT DOCUMENTS

| EP | 2833187 A1 | 2/2015 |
|---|---|---|
| EP | 2856924 A1 | 4/2015 |
| WO | WO 2015/194486 A1 | 12/2015 |

OTHER PUBLICATIONS

"Insertion Tube Rotation Function," www.olympus.it/medical/en/medical_systems/products_services/systems_1/evis_exera_iii/exera_iii_bf/exera_iii_bf_advancing_maneuverability.isp, last accessed Oct. 18, 2017.

*Primary Examiner* — John P Leubecker
*Assistant Examiner* — Minqiao Huang
(74) *Attorney, Agent, or Firm* — Bookoff McAndrews, PLLC (57) ABSTRACT

A medical device may include a handle having a first handle portion and a second handle portion. The first handle portion may be rotatable relative to the second handle portion. The medical device may also include a deflectable shaft coupled to and extending distally of the first handle portion. A port may be positioned on the first handle portion and a control knob may be coupled to the shaft.

15 Claims, 4 Drawing Sheets

(51) Int. Cl.
*A61B 1/015* (2006.01)
*A61B 1/307* (2006.01)
*A61B 17/00* (2006.01)

(56) References Cited

U.S. PATENT DOCUMENTS

| | | | |
|---|---|---|---|
| 7,736,301 B1* | 6/2010 | Webler | A61B 5/0062 |
| | | | 385/53 |
| 8,992,470 B2 | 3/2015 | Barenboym et al. | |
| 2006/0252996 A1* | 11/2006 | Goldfain | A61B 1/00188 |
| | | | 600/200 |
| 2009/0062615 A1 | 3/2009 | Yamaya | |
| 2010/0030031 A1 | 2/2010 | Goldfarb et al. | |
| 2016/0089127 A1* | 3/2016 | Kirkemo | A61B 17/221 |
| | | | 606/110 |
| 2017/0079520 A1 | 3/2017 | Huang et al. | |
| 2017/0086651 A1* | 3/2017 | Sato | A61B 1/00114 |
| 2017/0259043 A1* | 9/2017 | Chan | A61M 25/09 |

* cited by examiner

FIG. 6

MEDICAL SYSTEMS, DEVICES, AND RELATED METHODS

CROSS-REFERENCE TO RELATED APPLICATIONS

This patent application claims the benefit of priority under 35 U.S.C. § 119 to U.S. Provisional Patent Application No. 62/415,206, filed Oct. 31, 2016, which is herein incorporated by reference in its entirety.

TECHNICAL FIELD

Various aspects of the present disclosure relate generally to medical systems, devices, and related methods. More specifically, the present disclosure relates to medical systems and/or devices for selectively adjusting an angular orientation of a shaft.

BACKGROUND

Ureteroscopy may be performed to diagnose and treat urinary tract diseases and ureteral strictures. A ureteroscope may be inserted retrograde through the urinary tract such that diagnosis and treatment of urinary tract abnormalities may be performed. Current ureteroscopes generally require a medical professional to rotate his or her forearm to adjust the angular rotation of a ureteroscope which may result in awkward or challenging grasping of the ureteroscope. Additionally, rotation of the medical professional's forearm may comprise or inhibit intuitive control of the ureteroscope during a procedure.

The systems, devices, and methods of the current disclosure may rectify some of the deficiencies described above or address other aspects of the prior art.

SUMMARY

Examples of the present disclosure relate to, among other things, medical devices. Each of the examples disclosed herein may include one or more of the features described in connection with any of the other disclosed examples.

In one example, a medical device may include a medical device may include a handle having a first handle portion and a second handle portion. The first handle portion may be rotatable relative to the second handle portion. The medical device may also include a deflectable shaft coupled to and extending distally of the first handle portion. A port may be positioned on the first handle portion and a control knob may be coupled to the shaft.

Examples of the medical device may include one or more of the following features. The control knob may be coupled to the shaft distally of the distal end of the first handle portion. The control knob may include an alignment indicator indicative of an angular position of the shaft. The control knob may be longitudinally and rotationally fixed with respect to the shaft. The control knob may be selectively adjustable along the length of the shaft. The device may include a shaft deflection actuator, and the shaft deflection actuator may be coupled to the second handle portion. A proximal end of the first handle portion may be rotatably coupled to a distal end of the second handle portion. The control knob may include a collet and a sleeve. The collet may include a plurality of segments separated by a slit. At least one of the plurality of segments may include a ramp thereon. In an unlocked configuration, the sleeve may be positioned proximally of the ramp. In a locked configuration, the ramp may be received within a lumen of the sleeve. The port may include a T-port or a Y-port. The first handle portion may include a recess extending about an exterior circumferential surface of the first handle portion. The second handle portion may include at least one rib extending radially inwardly of an interior circumferential surface of the second handle portion, and the rib may be positioned within the recess of the first handle portion.

In a further example, a method of operating a medical device is described. The medical device may include a handle having a first handle portion which may be rotatable relative to a second handle portion and the first handle portion may include a port thereon. The method may include manipulating an actuator located on the second handle portion to deflect a shaft coupled to the first handle portion. Further, the method may include rotating a control knob coupled to the shaft so as to rotate first handle portion relative to second handle portion.

Examples of the method may further include one or more of the following features. Rotating the first handle portion relative to the second handle portion may include rotating a rib of the second handle portion within a recess of the first channel portion. The method may also include adjusting a location of the control knob along the shaft.

In a further example, a medical device may include a handle having a first handle portion and a second handle portion. The first handle portion may be rotatable relative to the second handle portion about a longitudinal axis of the first handle portion. A recess may extend about a surface of at least one of the first handle portion and the second handle portion. A rib may extend radially outwardly of a surface of another of the at least one of the first handle portion and the second handle portion. The rib may be positioned within the recess. A deflectable shaft may be coupled to and extend distally of the first handle portion and a port may be positioned on the first handle portion.

Examples of the medical device may include one or more of the following features. A control knob may be coupled to the shaft. The control knob may be adjustably positioned along the shaft. The first handle portion may include a proximal knob received within the second handle portion, and the proximal knob may be fluted. The second handle portion may include at least one window extending through a wall of the second handle portion. The knob of the first handle portion may be positioned at least partially within the at least one window of the second handle portion.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to medical systems and devices for diagnosing and/or treating internal areas of a subject's body. The medical system may include an insertion device and one or more medical devices operably coupled thereto for introduction of an end effector or other object through the insertion device.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively further away from the operator using the medical device or insertion device, or closer to the interior of the body.

Figures 1, 2:
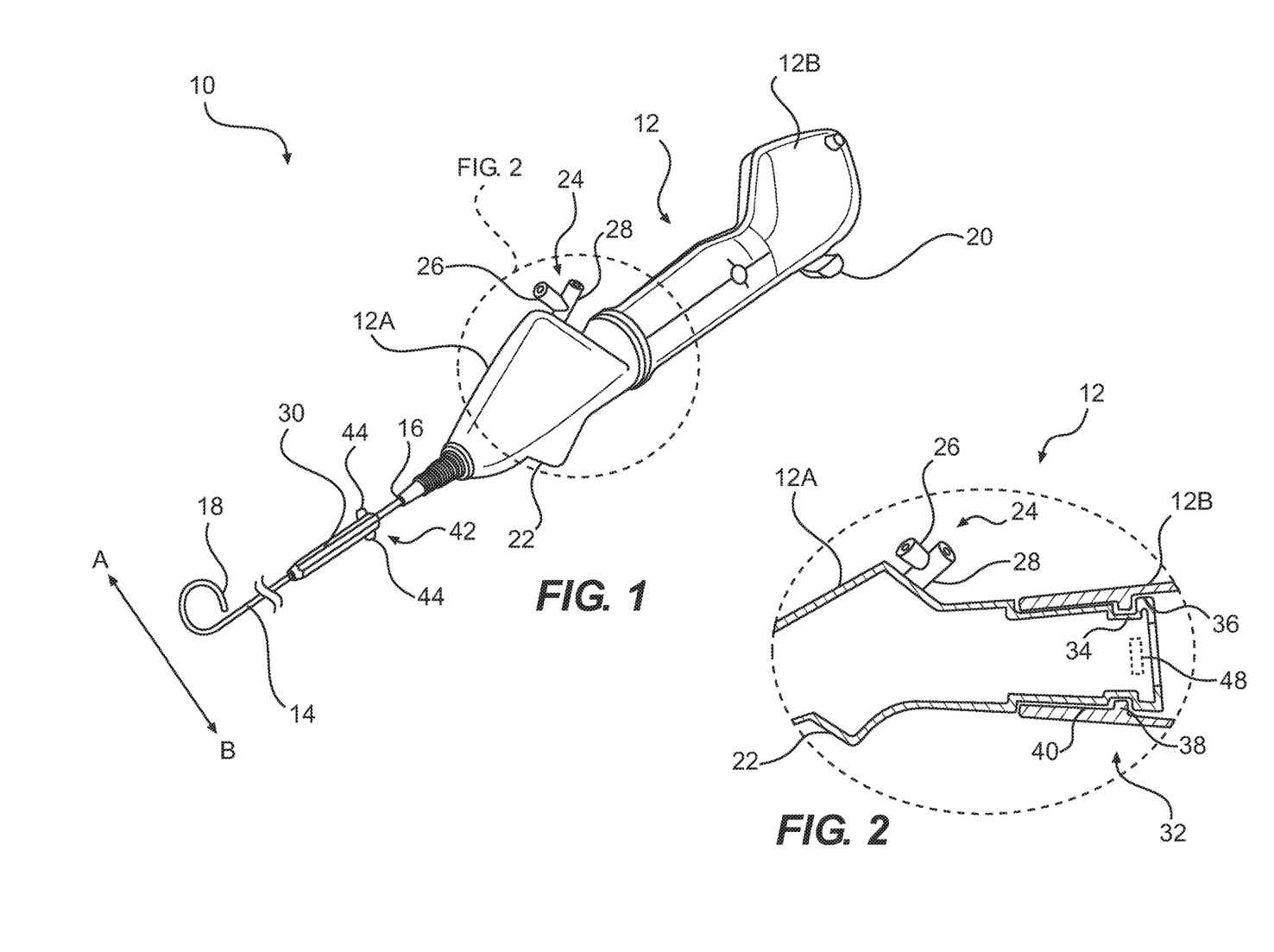
FIG. 1 illustrates an exemplary insertion device including a control knob.
FIG. 2 illustrates a partial cross-sectional side-view of the insertion device of FIG. 1.

FIG. 1 illustrates an exemplary insertion device 10 including a handle 12 coupled to a shaft 14. Insertion device 10 includes any device configured to allow an operator to perform medical diagnoses and/or treatments on a subject. For example, insertion device 10 includes any device configured to allow a user to access and view internal areas of a subject's body. Additionally or alternatively, insertion device 10 may itself be a medical device and/or include any device configured to deliver one or more medical devices, such as, for example, biopsy forceps, graspers, baskets, snares, probes, scissors, retrieval devices, lasers, and/or other tools, into a subject's body. Insertion device 10 may be inserted into one of a variety of body openings, lumens, and/or cavities. For example, insertion device 10 may be inserted into any portion of a urinary tract, such as a ureter, a gastrointestinal lumen, such as an esophagus, a vascular lumen, and/or an airway.

According to aspects of the present disclosure, insertion device 10 is a ureteroscope. In some contemplated examples, insertion device 10 is a sterile, single-use, and disposable ureteroscope. Alternatively, insertion device 10 is a multiple-use, non-disposable ureteroscope. Other types of devices, however, may be substituted for the ureteroscope, including, as examples, a hysteroscope, a uteroscope, a bronchoscope, a cystoscope, and similar devices. Such devices may be single-use and disposable, or multiple-use.

Handle 12 of insertion device 10 may have any shape suitable for gripping and controlling insertion device 10. For example, handle 12 may have an ergonomic shape designed to be held comfortably in the hand, e.g., the palm of the hand of a medical professional. Additionally, handle 12 includes a first handle portion 12A and a second handle portion 12B as shown in FIG. 1, and as will be described in further detail below. Shaft 14 may extend from a proximal end 16 to a distal end 18 such that proximal end 16 of shaft 14 is coupled to (e.g., detachably or permanently connected to) a distal end of handle 12. Insertion device 10 includes a steering mechanism for deflecting shaft 14 along one or more planes. For example, handle 12 includes an actuator 20 coupled to one or more portions of shaft 14 at or near distal end 18 via one or more control members, such as steering wires (e.g., Bowden cables, not shown). Any suitable steering mechanism and/or actuators may be used. Upon manipulation of actuator 20, a medical professional may selectively deflect distal end 18 of shaft 14 in a first direction A or a second direction B along a deflection plane transverse to the longitudinal axis of handle 12. As shown, actuator 20 may be located along an enlarged proximal end of handle 12. Such an enlargement may be useful to facilitate grasping of handle 12. For instance, when held upright, the enlarged proximal end of handle 12 may rest on a portion of the medical professional's hand so as to improve grasping of handle 12.

Shaft 14 includes at least one working channel (not shown) extending between proximal end 16 and distal end 18 of shaft 14. In some examples, shaft 14 may include one or more electronic components, such as a camera or other imaging device, a light source, and/or other sensor (not shown). Additionally or alternatively, shaft 14 may include a lumen for light delivery and/or steering control members (not shown) associated with actuator 20 for steering shaft 14.

Handle 12 also includes an umbilicus hub or connector 22 for facilitating electrical connections and functions, such as transferring data and/or powering a light source. In addition, handle 12 includes at least one port 24 (e.g., a T-shaped or Y-shaped luer port connection). Port 24 includes a first branch 26. First branch 26 may be fluidly coupled to one or more sources of irrigation and/or suction fluid. Accordingly, irrigation fluid (not shown) may be delivered (e.g., pumped) through the working channel via first branch 26 to provide lubrication and/or aid in visualization. Port 24 also includes a second branch 28 in communication with the working channel, e.g., to allow for the insertion of one or more medical device(s) through the working channel to distal end 18 of shaft 14. For example, second branch 28 may comprise a medical (e.g., threaded) or slip luer port through which an end effector, control member, and/or sheath of medical device (not shown) may be delivered into second branch 28 and the working channel.

As noted above, handle 12 includes first handle portion 12A and second handle portion 12B. First handle portion 12A is coupled to proximal end 16 of shaft 14 and is located distally of second handle portion 12B. As shown, connector 22 and port 24 are arranged or disposed on first handle portion 12A, while actuator 20 is located on second handle portion 12B. First handle portion 12A is rotatable with respect to second handle portion 12B. That is, during use, a medical professional may adjust the angular orientation of first handle portion 12A relative to second handle portion 12B. For example, a medical professional may grip second handle portion 12B with his or her first hand and hold handle 12 generally upright such that a longitudinal axis of handle 12 and his or her first forearm are generally parallel with a longitudinal axis of the medical professional's torso while standing. In such a manner, actuator 20 will be generally closer to the medical professional's head. If it is deemed necessary or desirable to rotate shaft 14 during a procedure, the medical professional may rotate first handle portion 12A with his or her second hand via a control knob 30 (as will be described in further detail below). Since first handle portion 12A is rotatable relative to second handle portion 12B, the medical professional is not required to rotate his or her first forearm or first hand to rotate shaft 14, thereby enabling consistent ergonomic grasping and intuitive control of insertion device 10 throughout a procedure.

As shown in FIG. 1, control knob 30 is coupled to shaft 14 distally of proximal end 16 of shaft 14. Control knob 30 is longitudinally and rotationally fixed with respect to shaft 14. For example, control knob 30 may be glued, welded, or otherwise fixedly coupled to shaft 14. Control knob 30 may have any suitable shape to facilitate ergonomic grasping and control of shaft 14. For example, as shown in FIG. 1, control knob 30 is ribbed or beveled similarly to a pencil shaft to improve a medical professional's grip on control knob 30. As shown, control knob 30 includes an alignment indicator 42. Alignment indicator 42 may be arranged anywhere along the length of control knob 30. For example, alignment indicator 42 is positioned at a proximal end of control knob 30, as shown in FIG. 1. Alignment indicator includes one or more extensions, protrusions, or tabs 44 extending radially outwardly from control knob 30. Such tabs 44 may facilitate proper orientation of shaft 14. For example, as shown in FIG. 1, tabs 44 are aligned so as to extend along the deflection plane (as noted above). That is, a first tab 44 extends in direction A while a second tab 44 extends in direction B along the deflection plane. In such a manner, the radial orientation of shaft 14 may be readily ascertained by observing or feeling the orientation of tabs 44.

To facilitate rotation of first handle portion 12A relative to second handle portion 12B, handle 12 may be arranged as shown in the partial cross-sectional view of FIG. 2. For example, first handle portion 12A and second handle portion 12B overlap one another so as to form a rotatable joint 32. To facilitate rotation, at least the overlapping portions of first handle portion 12A and second handle portion 12B may have a common cross-sectional shape (e.g., circular).

As shown, a proximal end of first handle portion 12A is moveably (e.g., rotatably) received within a distal portion of the second handle portion 12B such that first handle portion 12A may be rotatable about a longitudinal axis of first handle portion 12A and relative to second handle portion 12B. Alternatively, a distal portion of the second handle portion 12B may be moveably (e.g., rotatably) received within a proximal end of first handle portion 12A such that first handle portion 12A may be rotatable about a longitudinal axis of first handle portion 12A and relative to second handle portion 12B.

First handle portion 12A includes a channel, groove, or recess 34 extending circumferentially about or around an exterior circumferential surface 36 of first handle portion 12A. Additionally, second handle portion 12B includes one or more protrusions, extensions, or ribs 38 arranged within recess 34. Rib(s) 38 may be a single continuous rib extending radially inwardly and about an entire circumferential interior surface 40 of second handle portion 12B. Alternatively, rib(s) 38 may extend about less than the entire circumferential interior surface 40 of second handle portion 12B. Any desired number or arrangement of rib(s) 38 (e.g., equidistantly spaced or non-equidistantly spaced) about the circumferential interior surface 40 and positioned within recess 34, is envisioned.

During rotation of first handle portion 12A relative to second handle portion 12B, interaction between rib(s) 38 and recess 34 maintains coupling of first handle portion 12A and second handle portion 12B together while enabling angular rotation therebetween. It is understood that in some aspects, second handle portion 12B may include recess 34 while first handle portion 12A includes rib(s) 38 without departing from the scope of this disclosure. Additionally, other rotational coupling mechanisms may be used without departing from the scope of this disclosure. Further, it is understood that one or more components of handle 12 (e.g., recess 34 and/or rib(s) 38) may be lubricated to facilitate smooth rotation of first handle portion 12A relative to second handle portion 12B. For example, a PTFE gasket (not shown) may be included to provide both lubrication and sealing between components of handle 12. In some arrangements in which rib 38 does not extend around the entire circumferential interior surface 40 of second handle portion 12B, a stop 48 may be located along recess 34 to limit rotation between first handle portion 12A and second handle portion 12B, as will be described in further detail below.

Figure 3A:
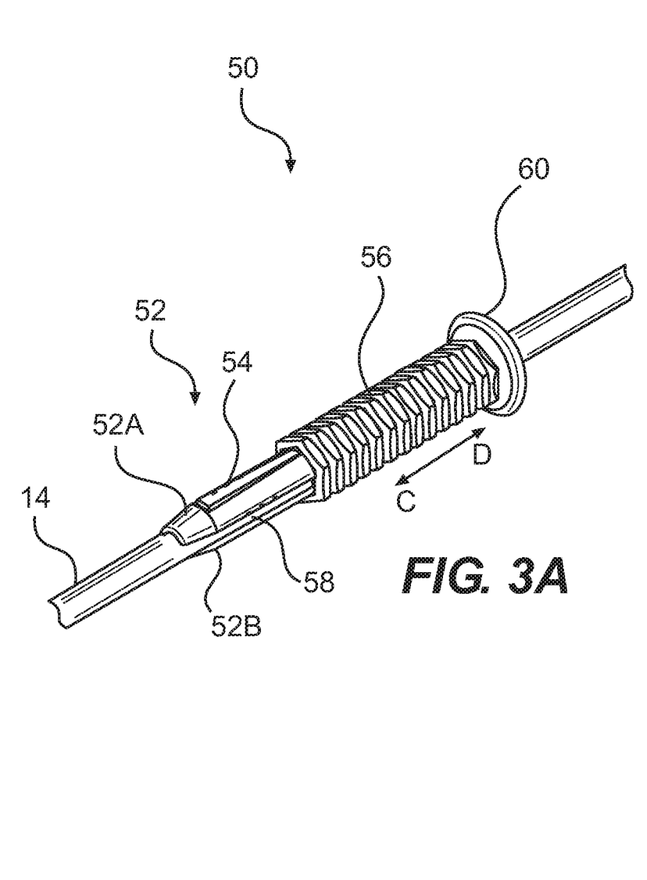
FIGS. 3A and 3B illustrate views of an additional control knob according to aspects of the present disclosure.
Figure 3B:
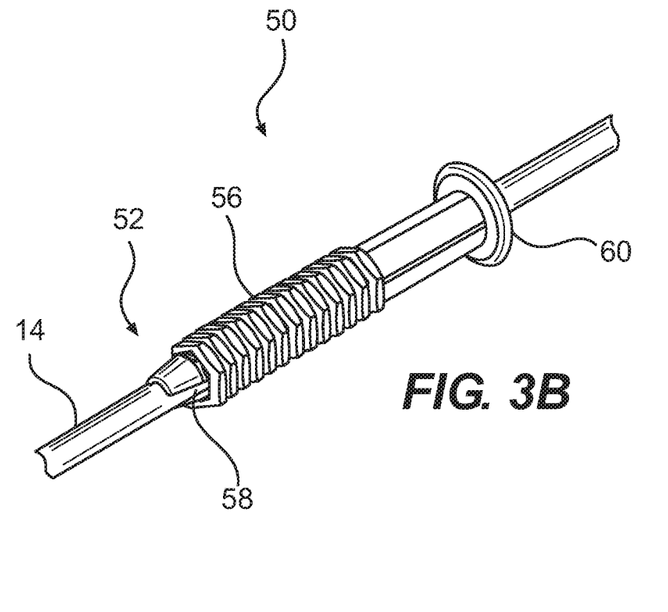

FIGS. 3A and 3B illustrate an alternative exemplary control knob 50. Control knob 50 may serve a similar purpose to control knob 30. However, unlike control knob 30, control knob 50 may be longitudinally adjustable along shaft 14. That is, control knob 50 may be selectively positioned along the length of shaft 14 to enable effective and intuitive control of shaft 14. Control knob 50 includes a collet 52 having at least one ramp 54 and a moveable sleeve 56 having a lumen extending therethrough. As shown, collet 52 includes a proximal stop 60 and a plurality radially adjustable segments 52A and 52B separated by one or more slits 58. While only two segments 52A and 52B are shown, it is understood that any number of segments may be used such as, e.g., between about two and about ten segments. At least one or more expandable segment 52A and 52B includes ramp 54 thereon. For example, as shown in FIGS. 3A and 3B, segment 52A includes a ramp 54 thereon. Each ramp 54 has a distal portion that extends radially outwardly of a respective segment 52A and 52B than a proximal portion. That is, each ramp 54 is angled with respect to a respective segment 52A and 52B.

Slit 58 enables segments 52A and 52B to spread radially away from one another (e.g., away from a longitudinal central axis of collet 52). Once spread apart, collet 52 may be selectively moved distally or proximally along the length of shaft 14. In order to lock or secure control knob 50 at a selected location along shaft 14, sleeve 56 may be moved from an unlocked configuration, as shown in FIG. 3A, towards a locked configuration, as shown in FIG. 3B. To do so, the medical professional may distally advance (e.g., slide) sleeve 56 towards the distal end of collet 52 in the direction C, and over segments 52A and 52B. As sleeve 56 is moved distally, an internal surface of sleeve 56 engages and moves along each ramp 54. As sleeve 56 engages and moves along ramp 54, the internal surface of sleeve 56 will progressively compress or urge each segment 52A and 52B radially inwards toward one another so as to reduce the size of slit 58 and pinch or grip shaft 14. Indeed, in some arrangements, sleeve 56 may be advanced in the direction C until a distal end of sleeve 56 is secured against a distal surface of ramp 54 and may optionally provide an audible indication (e.g., clicking) of proper coupling therebetween. In such a manner, control knob 50 may be secured longitudinally with respect to shaft 14. To unlock control knob 50, the medical professional may retract sleeve 56 proximally in the direction D to release sleeve 56 from each ramp 54, thereby enabling segments 52A and 52B to expand radially outwardly away from shaft 14. Alternative securing mechanisms may include a compressing grommet and/or a locking ferrule. As shown, sleeve 56 may be knurled, textured, or otherwise ribbed to facilitate secure grasping thereof. Additionally, proximal stop 60 may include an alignment indicator (not shown) similar to alignment indicator 42. As such, stop 60 may additionally or alternatively include tabs 44 and or indicia indicative of an angular orientation of shaft 14.

As such, each of control knob 30 and control knob 50 may be secured to shaft 14. In use, if the medical professional determines a need or desire to rotate shaft 14, he or she may grasp and rotate control knob 30 or 50 coupled to shaft 14. As shaft 14 is coupled to first handle portion 12A, rotation of shaft 14 will cause likewise rotation of first handle portion 12A. However, due to rotational joint 32, rotation of first handle portion 12A may not necessarily result in rotation of second handle portion 12B. As such, a medical professional may use control knob 30 or 50 to rotate shaft 14 and first handle portion 12A with one hand (e.g., their non-dominate hand) without necessitating rotation of the second handle portion 12B with another hand and forearm (e.g., their dominate hand and forearm). Accordingly, consistent ergonomic grasping and intuitive control of insertion device 10 throughout a procedure may be achieved. Moreover, due to the grasping of control knob 30 or 50, a medical professional does not need to grasp first handle portion 12A to rotate shaft 14. As such, interference with fluid supply lines and/or medical devices coupled to port 24 may be avoided.

Figure 4:
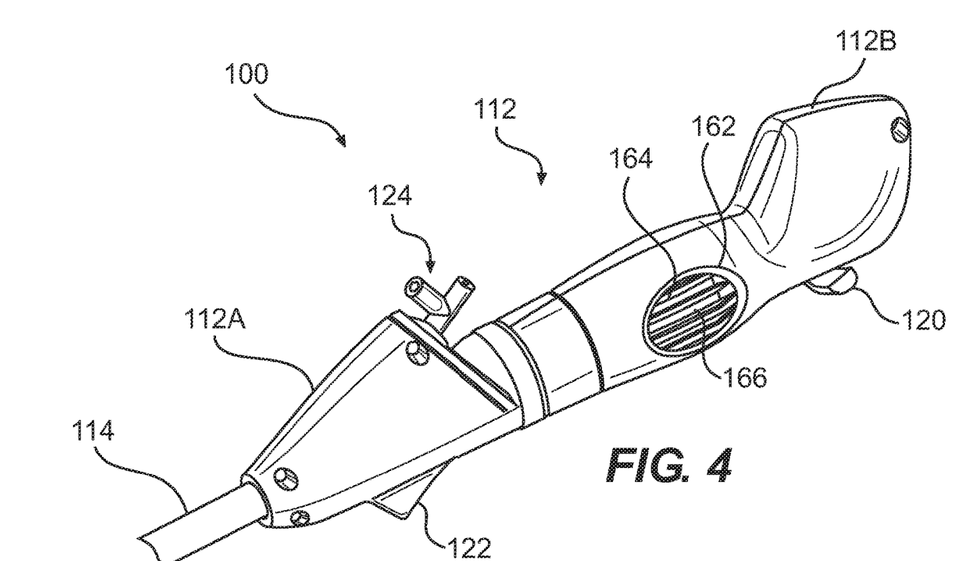
FIG. 4 illustrates an additional exemplary insertion device according to aspects of the present disclosure.

FIG. 4 illustrates an additional exemplary insertion device 100. Insertion device 100 may be similar to insertion device 10 and as such, like parts are denoted by the same reference numerals plus 100. For example, insertion device 100 includes a handle 112 having a first handle portion 112A and a second handle portion 112B. First handle portion 112A may be located distally of second handle portion 112B and rotatable relative thereto, as will be described in further detail below. Similar to first handle portion 12A, first handle portion 112A includes a connector 122 and port 124. Additionally, similar to second handle portion 12B, second handle portion 112B includes an actuator 120 thereon. Further, insertion device 100 may be arranged for one-handed (e.g., only one hand) control thereof, as will be described in further detail below.

Figure 5:
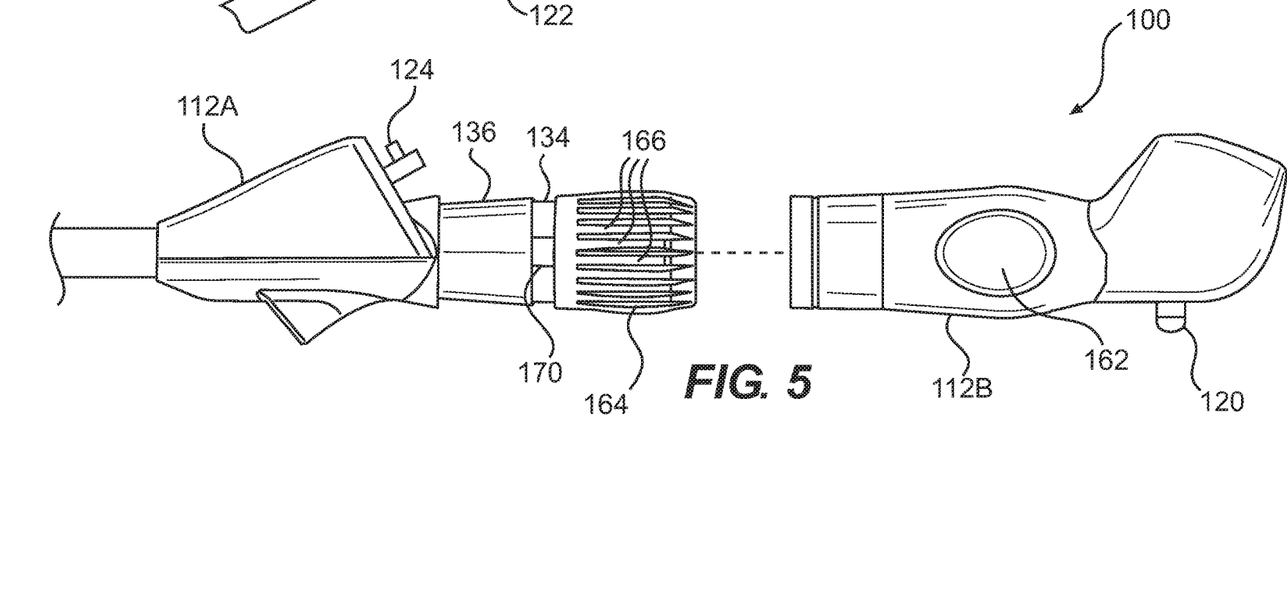
FIG. 5 illustrates an exploded view of the insertion device of FIG. 4.
Figure 6:
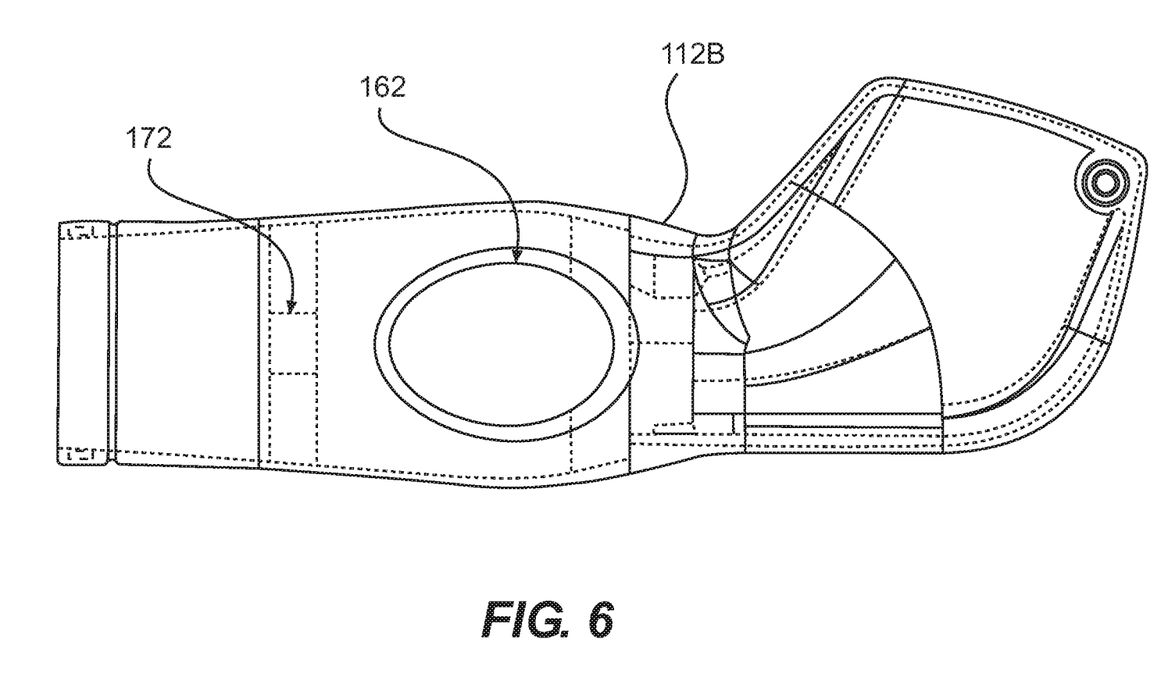
FIG. 6 illustrates a partial cross-sectional view of a portion of the insertion device of FIG. 4.

As shown in FIG. 4, second handle portion 112B may include at least one window 162 extending through a wall (e.g., a lateral side wall) of second handle portion 112B. While only a single window 162 is shown in FIGS. 4-6, second handle portion 112B may include any number of windows 162. For example, second handle portion 112B may include a pair of windows 162 on opposite sides of second handle portion 112B. Additionally, while window 162 is depicted as being located on a side or lateral surface of second handle portion 112B, such a location is merely exemplary. In other arrangements, window 162 may be located at any location about the circumference of second handle portion 112B. For example, window 162 may be arranged along a top or bottom surface (e.g., any location 90° displaced from the location depicted in FIGS. 4-6 about the circumferential surface of second handle portion 112B). Window 162 may be located along second handle portion 112B so as to be adjacent actuator 120. That is, window 162 may be located along handle portion 112B such that a medical professional holding handle 112 may be able to manipulate actuator 120 with their thumb or a finger of their first (e.g., dominate) hand and wrap one or more of their remaining fingers around the circumference of second handle portion 112B such that at least one of their fingers on their first (e.g., dominate hand) may be located over window 162 to rotate knob 164 (as will be described in further detail below). As shown in FIGS. 4-6, window 162 may be generally ovular. However, other shapes of window 162 may be used without departing from the scope of the disclosure. For example, window 162 may have a circular, polygonal, or irregular shape.

First handle portion 112A may include a proximal end including a knob 164. At least knob 164 may be received within second handle portion 112B. That is, as shown in FIG. 4, knob 164 of first handle portion 112A may located within second handle portion 112B so as to be visible through window 162. In order to facilitate insertion, second handle portion 112B may be a clam shell arrangement in which two halves of second handle portion 112B may be separated to receive knob 164 therein. After placement of knob 164 between the halves of second handle portion 112B, the halves of second handle portion 112B may be coupled together, as shown in FIG. 4. Additionally, as shown, knob 164 includes ribs or flutes 166 thereon which may facilitate secure gripping or placement of one or more fingers of the medical professional thereon.

As shown in FIG. 5, first handle portion 112A includes a recess 134 distally of knob 164. Recess 134 may be similar to recess 34, described above. As such, recess 166 extends circumferentially about or around an exterior circumferential surface 136 of first handle portion 112A. A first stop 170 is located within recess 134. First stop 170 may be a protrusion or extension arranged for cooperation with a second stop 172 (FIG. 6) located along a circumferential interior surface (not shown) of second handle portion 112B. For example, one or both of first stop 170 and second stop 172 include a protrusion or extension. Second stop 172 is sized and shaped to be received within recess 166 such that interaction between second stop 172 and recess 134 maintains coupling of first handle portion 112A and second handle portion 112B together while enabling angular rotation therebetween. It is understood that the stops 170 and 172 may be sized and/or shaped so as to maintain sufficient coupling between first handle portion 112A and second handle portion 112B. Additionally, interaction between first stop 170 and second stop 172 limits the degree of rotation between first handle portion 112A and second handle portion 112B. That is, during use, the medical professional may rotate first handle portion 112A relative to second handle portion 112B until first stop 170 contacts second stop 172 at which point, further rotation of first handle portion 112A in the same direction is prevented. Additionally, while not illustrated, control knob 30 (FIG. 1) or control knob 50 (FIGS. 3A and 3B) may optionally be located on shaft 114 without departing from the scope of the instant disclosure. Further, one or more components of handle 112 (e.g., recess 134 and/or stops 170 and 172) may be lubricated to facilitate smooth rotation of first handle portion 112A relative to second handle portion 112B. In use, the medical professional may rotate shaft 114 by rotating knob 164 with one or more fingers of their dominate hand while their thumb or another finger remains on or adjacent actuator 120. In such a manner, single-handed (e.g., only one hand) operation of handle 12 may be achieved.

In such a manner, each of insertion device 10 and insertion device 100 enables rotation between a first handle portion 12A, 112A, and a second handle portion 12B, 112B to facilitate ergonomic and intuitive control of handle 12, 112 without necessitating awkward positioning of the medical professional's hand and/or forearm. That is, as discussed above, if it is determined during a procedure to be necessary or desired to rotate shaft 14, 114 (e.g., to reach a different location), such rotation may be accomplished via control knob 30, 50 and/or knob 164 such that the medical professional is not required to rotate the entirety of handle 12, 112 or their dominate hand or forearm. Instead, shaft 14, 114 may be rotated via rotation of control knob 30, 50, or knob 164. In such a manner, a medical professional may avoid grasping first handle portion 12A to rotate shaft 14, thereby preventing interference with fluid supply lines and/or medical devices coupled to port 24 or 124. Further, the medical professional may insert, withdraw, and rotate shaft 14, 114 without repositioning their hand. Additionally, in instances in which knob 164 is used, single-handed operation of handle 112 may be achieved thereby freeing the medical professional's other hand for different tasks.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

I claim:

1. A medical device, comprising:
a handle having a first handle portion and a second handle portion, wherein the first handle portion is rotatable relative to the second handle portion;
a deflectable shaft coupled to and extending distally of the first handle portion;
a port positioned on the first handle portion; and
a control knob coupled to the shaft,
wherein the deflectable shaft is rotatable relative to the second handle portion,
wherein the control knob includes a collet and a sleeve, the collet includes a plurality of segments separated by a slit, and at least one of the plurality of segments includes a ramp thereon.

2. The device of claim 1, wherein the control knob is coupled to the shaft distally of a distal end of the first handle portion.

3. The device of claim 2, wherein the control knob includes an alignment indicator indicative of an angular position of the shaft.

4. The device of claim 1, wherein the control knob is longitudinally and rotationally fixed with respect to the shaft.

5. The device of claim 1, wherein the control knob is selectively adjustable along the length of the shaft.

6. The device of claim 1, wherein, in an unlocked configuration, the sleeve is positioned proximally of the ramp.

7. The device of claim 6, wherein, in a locked configuration, the ramp is received within a lumen of the sleeve.

8. The device of claim 1, wherein the first handle portion includes a recess extending about an exterior circumferential surface of the first handle portion, the second handle portion includes at least one rib extending radially outwardly of an interior circumferential surface of the second handle portion, and wherein the rib is positioned within the recess of the first handle portion.

9. A method of operating the medical device of claim 1, the method comprising:
manipulating an actuator located on the second handle portion to deflect the shaft coupled to the first handle portion; and
rotating the control knob coupled to the shaft so as to rotate the first handle portion relative to the second handle portion.

10. The method of claim 9, wherein rotating the first handle portion relative to the second handle portion includes rotating a rib of the second handle portion within a recess of the first channel portion.

11. The method of claim 9, further including adjusting a location of the control knob along the shaft.

12. A medical device, comprising:
a handle having a first handle portion and a second handle portion;
a deflectable shaft extending distally from the first handle portion, wherein a proximal end of the deflectable shaft is coupled to a distal end of the first handle portion;
a port positioned on the handle; and
a control knob rotationally fixed to the shaft,
wherein the first handle portion and the deflectable shaft are rotatable relative to the second handle portion, and
wherein the control knob includes a collet and a sleeve, the collet includes a plurality of segments separated by a slit, and at least one of the plurality of segments includes a ramp thereon.

13. The device of claim 12, wherein the control knob is selectively adjustable along the length of the shaft.

14. The device of claim 12, wherein, in an unlocked configuration, the sleeve is positioned proximally of the ramp.

15. The device of claim 12, wherein, in a locked configuration, the ramp is received within a lumen of the sleeve.

\* \* \* \* \*